US006156174A

United States Patent [19]

Baerts et al.

[11] Patent Number: 6,156,174

[45] Date of Patent: Dec. 5, 2000

[54] IMMERSION SENSOR FOR MEASURING AN ELECTROCHEMICAL ACTIVITY

[75] Inventors: Christiaan Baerts, Beringen-Paal; Guido Neyens, Maaseik/Opoeteren, both of Belgium

[73] Assignee: Heraeus Electro-Nite International N.V., Houthalen, Belgium

[21] Appl. No.: 09/439,184

[22] Filed: Nov. 12, 1999

Related U.S. Application Data

[62] Division of application No. 09/132,656, filed as application No. PCT/EP97/06920, Dec. 11, 1997, Pat. No. 5,989,408.

[30] Foreign Application Priority Data

Dec. 18, 1996 [DE] Germany .......................... 196 52 596

[51] Int. Cl.[7] .................................................. G01N 27/411

[52] U.S. Cl. ............................................ 204/423; 204/422

[58] Field of Search .................................... 204/422, 423; 205/783.5, 784

[56] References Cited

U.S. PATENT DOCUMENTS

| | | |
|---|---|---|
| 3,298,944 | 1/1967 | Luck ....................................... 204/435 |
| 3,630,874 | 12/1971 | Olette et al. . |
| 3,838,021 | 9/1974 | Arbiter . |
| 3,864,231 | 2/1975 | Richardson . |
| 4,639,304 | 1/1987 | Bader et al. . |
| 4,657,641 | 4/1987 | Nakamura et al. . |
| 5,445,725 | 8/1995 | Koide et al. . |
| 5,792,329 | 11/1998 | Cure et al. . |

FOREIGN PATENT DOCUMENTS

| | | |
|---|---|---|
| 0 330 264 A1 | 8/1989 | European Pat. Off. . |
| 0 450 090 A1 | 10/1991 | European Pat. Off. . |

*Primary Examiner*—T. Tung

*Attorney, Agent, or Firm*—Akin, Gump, Strauss, Hauer & Feld, L.L.P.

[57] ABSTRACT

A process as well as an immersion sensor for measuring an electrochemical activity of a layer lying on a melt is provided, using an electrochemical sensor, which has a measuring cell and a counter electrode. In order to make possible reliably reproducible and accurate measurements in the layer, the measuring cell and counter electrode are first immersed in the melt, wherein the measuring cell and counter electrode are protected from contact with the layer and wherein the measuring cell and counter electrode are brought into contact with the melt and are heated. After that, the measuring cell is pulled up to perform the measurement in the layer, wherein the counter electrode is located in the melt during the measurement. For this purpose, the measuring cell and the counter electrode have a protective cover, and the measuring cell is arranged, in the immersion position of the sensor, above the counter electrode.

6 Claims, 4 Drawing Sheets

1
7
5
8
6
4
7

IMMERSION SENSOR FOR MEASURING AN ELECTROCHEMICAL ACTIVITY

CROSS-REFERENCE TO RELATED APPLICATION

This application is a divisional of U.S. application Ser. No. 09/132,656, filed Aug. 12, 1998, now U.S. Pat. No. 5,989,408 which in turn is a continuation of PCT/EP97/06920, filed Dec. 11, 1997, the disclosure of which is incorporated herein by reference.

BACKGROUND OF THE INVENTION

The invention involves a process for measuring an electrochemical activity of a layer lying on a melt (molten mass or bath), using an electrochemical sensor which has a measuring cell and a counter electrode.

Furthermore, the invention involves an immersion sensor for measuring an electrochemical activity of a layer lying on a melt, using an electrochemical sensor which is arranged on a support and has an electrochemical measuring cell and a counter electrode.

A process of this type and an immersion sensor of this type are known from *Radex-Review*, Issue 1, 1990, pages 236–243. A measuring process for measuring electrochemical activities, especially of the oxygen content of slag layers lying on iron melts, is described therein. The measurement is done by a conventional electrochemical sensor, which has a measuring cell with zirconium oxide and magnesium oxide as electrolytes and a counter electrode, arranged in the liquid slag layer. In particular, caused by non-homogenieties in the slag, the contact of the sensor with the material to be measured is not exactly defined, so that the measurement result cannot be reproduced with sufficient accuracy.

A similar sensor is described EP 330 264 A1. This sensor is used to determine the bath surface level, wherein the phase boundary between the metal melt and a slag layer lying on the metal melt is determined. A process for the indirect measurement of electrochemical activities in slags on silver melts is described in EP 0 450 090 B1. In this process, an electrochemical measuring cell is arranged in a silver melt. From the measurement, a conclusion is made about the activity in the slag.

SUMMARY OF THE INVENTION

Taking the known state of the art as a starting point, the purpose of the invention is to provide a process of the generic type, with which reliably reproducible and accurate measurements are possible in the layer. Furthermore, the purpose of the invention is to provide an immersion sensor suited to performing the process.

According to the invention, the purpose with regard to the process is achieved in that the measuring cell and the counter electrode are first immersed in the melt, wherein the measuring cell and the counter electrode are protected from contact with the layer, that the measuring cell and counter electrode are brought into contact with the melt and are heated (to approximately the temperature of the melt), that after that the measuring cell is pulled up into the layer in order to perform the measurement, and that the counter electrode is located in the melt during the measurement. In this way, the measurement takes place in the mostly liquid layer, after a temperature equilibration of the sensor to the surrounding temperature occurs.

The adjustment of the temperature is necessary, among other things, in order to prevent the material of the layer from solidifying on a sensor which is too cold. During the immersion of the sensor through the layer, the measuring cell and the counter electrode are protected against contact with the material of the layer by conventional protective covers which dissolve in the melt. The temperature adjustment can be monitored via the oxygen activity measurement. When an activity plateau, which is obtained in the melt after immersion, has been reached in the measurement curve, the temperature adjustment takes place. A monitoring of this adjustment is also possible using a thermo-element. The counter electrode is arranged in the melt during the measurement, i.e. in an exactly defined surrounding, making possible accurate and easily reproducable measurement values.

Expediently, the measuring cell and the counter electrode can be arranged on a support, whereby the counter electrode is simultaneously pulled up with the measuring cell. In this way, when the counter electrode is pulled back to the (liquid) layer, the electrochemical activity is measured. The bath surface level of the melt can be determined thereby, since an abrupt change of the electrochemical activity is measured as soon as the counter electrode reaches the boundary layer between the melt and the (liquid) layer lying on it. Advantageously, the temperature of the melt and/or the layer is determined during measurement.

It is also expedient that the measurement takes place during the lifting movement (the withdrawal movement) of the measuring cell and the counter electrode. In particular, it is also sensible to determine the oxygen activity of the melt prior to the withdrawal of the measuring cell from the melt. In this manner as well, the electrochemical activity, especially the oxygen activity of the melt and the layer lying on it, can be determined, and in the same measurement cycle the bath temperature and the bath surface level (boundary surface between the melt and the layer lying above it) can be determined using a single sensor, so that a separate measurement using another sensor is superfluous.

The measurement in the melt and/or in the layer can also be carried out during an interruption of the lifting movement of the immersion sensor, whereby the measuring cell and the counter electrode are located in the melt for measurement of the oxygen content or another electrochemical activity of the melt, while the measuring cell is located in the layer for measuring the oxygen content of the layer at the same time, wherein the counter electrode is arranged in the melt.

In an advantageous way, the process according to the invention can be implemented for measurement in a steel melt as well as the slag layer lying above it. The process can also be carried out for measurement in liquid glass and the layers lying above it. By melt, in the context of the invention, a metal melt or a glass melt or liquid glass is therefore to be understood. The determination of the oxygen activity in a slag layer lying on a steel melt also allows conclusions to be made about the content of other slag components besides iron oxide. This is, for example, presented in detail in the prior art described above.

The purpose is achieved for an immersion sensor according to the invention in that the measuring cell and the counter electrode have a protective cover, and that the measuring cell is arranged, in the immersion position of the sensor, above the counter electrode. A fixed distance between the measuring cell and the counter electrode is thereby given, and a simultaneous movement of the measuring cell and counter electrode occurs, such that the distance between the two of them is kept constant.

It is expedient if the support is constructed as a support tube, and the measuring cell is arranged on or in the side wall of the support tube, and the counter electrode is arranged on the front end of the support tube. It is also advantageous if the measuring cell is arranged in an opening in the side wall of the support tube. In another advantageous embodiment the measuring cell as well as the counter electrode are arranged on the immersion end of the support tube, such that the counter electrode is arranged on a holder which is affixed to the immersion end of the support tube, so that its active part has the necessary spacing from the measuring cell. Furthermore, it is advantageous in order to obtain an optimal measurement result, that the longitudinal axis of the measuring cell is arranged perpendicular to the longitudinal axis of the support tube. As is sufficiently known and described in detail in the literature, measuring cells of this type are generally constructed as tubes which are closed on one side and made of a solid electrolytic material, in which the reference electrode is arranged in a reference material.

It is further expedient if the distance between the measuring cell and the counter electrode (in the longitudinal direction) amounts to at least 2 cm. since by this spacing a tolerance range is taken into account which has the largest possible safety and results from a transition region between the melt and the layer lying on it. It is thereby ensured that the counter electrode can actually be arranged in the melt during measurement of the layer. It is further expedient if, on the immersion end of the support a thermo-element is arranged, in order to determine the temperature of the melt in a simple way.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
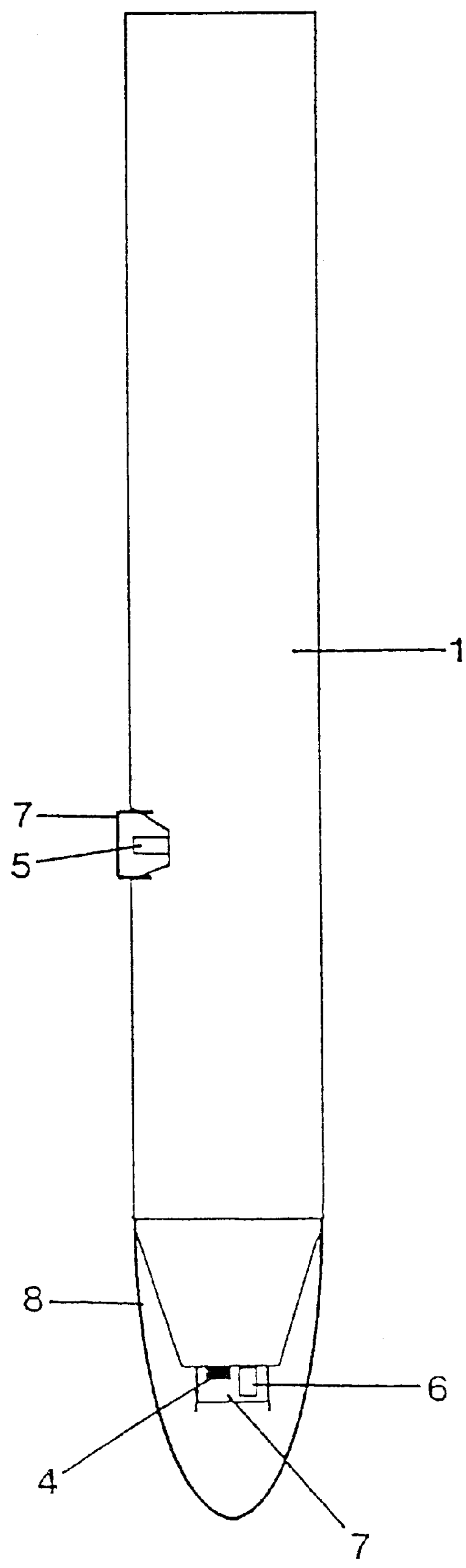
FIG. 1 is an immersion sensor having a measuring cell arranged on the side.
Figure 3:
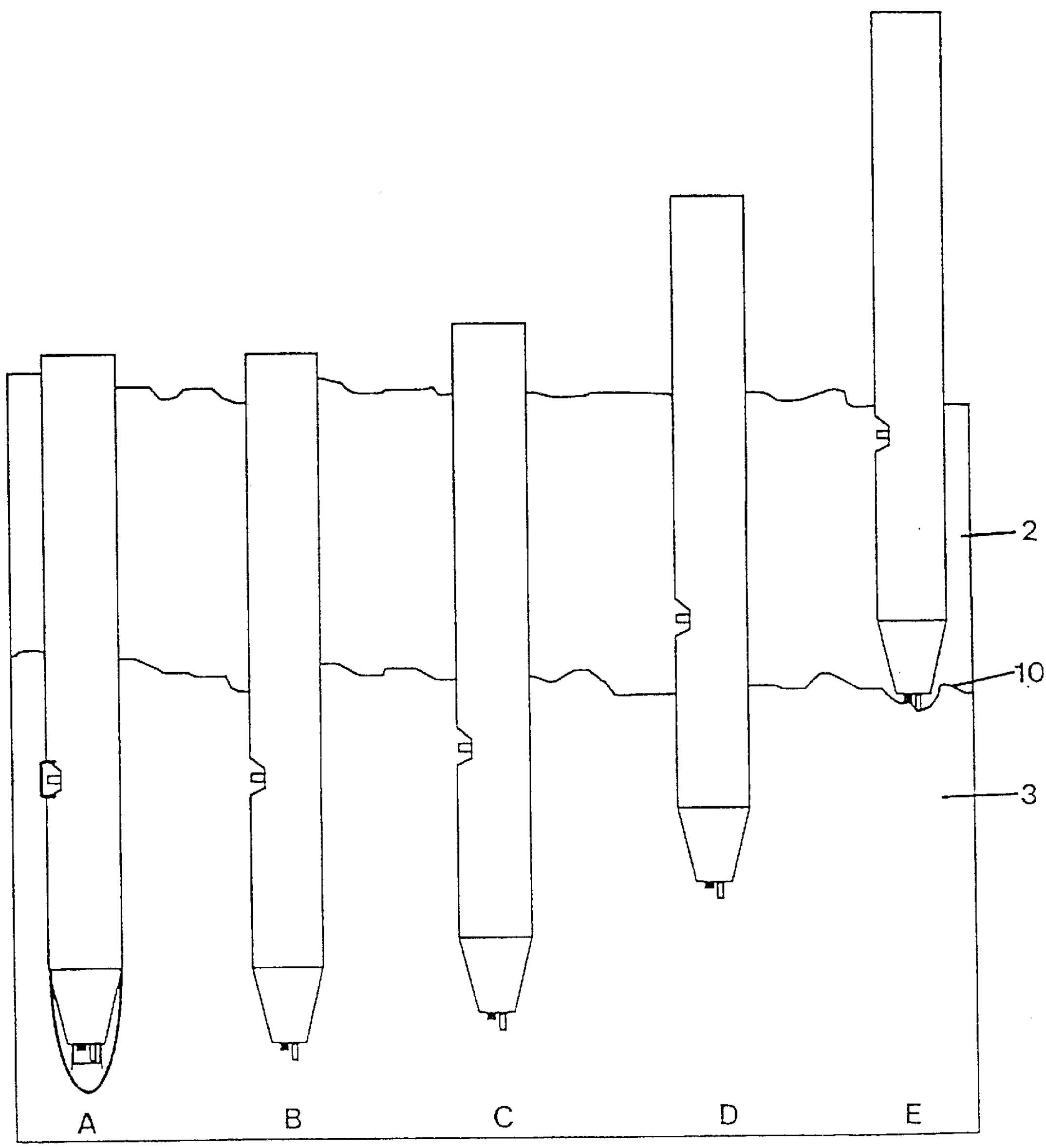
FIG. 3 is a schematic representation of the measuring process showing different positions of the immersion sensor.

The immersion sensor depicted in FIG. 1 has a support tube 1, on which an electrochemical sensor is arranged for measurement in a slag layer 2 above a steel melt 3 (See FIG. 3). Measurement conducting lines lead from the electrochemical sensor through the support tube 1, and a conventional lance attached for application onto the support tube 1, to evaluating devices. The electrochemical sensor, which has a measuring cell 5 and a counter electrode 4, is then protected by conventional protective covers 7 over the counter electrode 4 and the measuring cell 5. The protective covers 7 can comprise, for example, cardboard or metal or a combination of both materials. The immersion end of the support tube 1 is, in addition, protected by a metal cover 8. The counter electrode 4 is arranged on the immersion end of the support tube 1 of the sensor, while the measuring cell 5 is arranged several centimeters above the counter electrode 4 (in the immersion direction). In the surrounding area of the counter electrode 4, a thermo-element 6 is arranged. The counter electrode 4 can be constructed in a ring shape. The thermo-element 6 can then be arranged inside this ring-shaped counter electrode 4, and thereby mechanically protected by the counter electrode 4. The thermo-element 6 measures the temperature in the immediate vicinity of the counter electrode 4.

Figure 2:
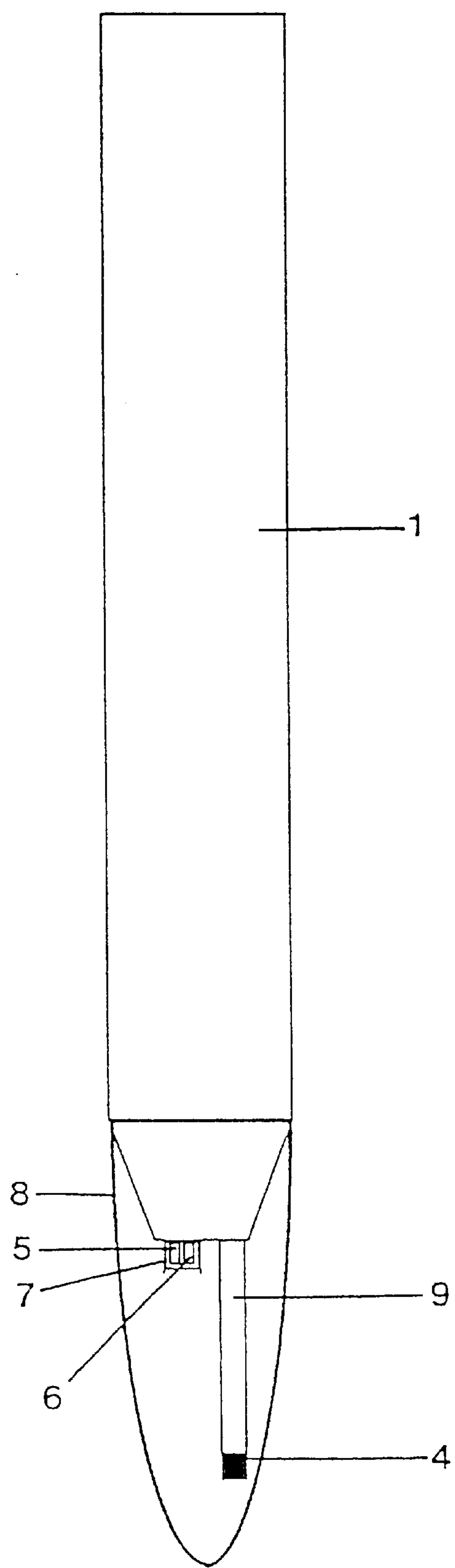
FIG. 2 is an immersion sensor having a measuring cell arranged on the front end.

FIG. 2 shows another possibility for constructing the electrochemical sensor in which the measuring cell 5 and the counter electrode 4 are mounted on the immersion end of the support tube 1. The measuring cell 5 is surrounded by a protective cover 7, inside of which a thermo-element 6 is also arranged and which effects a mechanical protection. The counter electrode 4 has a 40 cm spacing from the measuring cell 5 and is arranged at the end of a holder 9, which is attached to the immersion end. In this way, the counter electrode 4 located at its tip has a sufficient spacing from the measuring cell 5. The holder 9 can be a tube, through which the connection lines of the counter electrode are conducted in an insulated manner. The counter electrode 4 and the measuring cell 5 are thereby protected by a common protective cover 8.

It is also conceivable that the counter electrode 4 is not arranged on the support tube 1, but instead on the crucible which contains the steel melt 3, for example, on its bottom. In this case, a protective cover is not necessary, since the counter electrode 4 does not come into contact with the slag layer 2 (though the electrolyte level cannot be determined with this arrangement).

In order to perform the measurement, the electrochemical sensor is first immersed through the slag layer 2 into the steel melt 3 in such a way that both the counter electrode 4 as well as the measuring cell 5 are arranged within the steel melt 3. When passing through the slag layer 2, the sensor is protected by the protective covers 7; 8 from contacting and adhering to the slag. This condition is indicated in FIG. 3 as position A. In the steel melt 3 the sensor is heated, so that a temperature adjustment to the steel melt 3 occurs. The protective covers 7; 8 are dissolved in the process (position B). In the position C depicted in FIG. 3, the oxygen activity (the oxygen content) of the steel melt 3 is measured at first. After that, the electrochemical sensor is withdrawn upwardly until the measuring cell 5 is located above the steel melt 3 in the slag layer 2. Here, the oxygen activity in the slag layer 2 is measured, either during the upward movement or during a standstill of the sensor (position D).

The sensor is subsequently pulled further upwardly out of the steel melt 3. As soon as the counter electrode 4 also leaves the steel melt 3, i.e. enters into the boundary layer 10 between the steel melt 3 and the slag layer 2, the voltage measured in the measuring process increases abruptly, so that the boundary layer 10 between the steel melt 3 and the slag layer 2, i.e. the bath surface level of the metal bath (steel melt 3) is clearly shown (position E).

The distance between the counter electrode 4 and the measuring cell 5 is chosen to be larger than the thickness of the boundary layer 10 between the slag layer 2 and the steel melt 3; approximately 2 cm distance will be sufficient in some cases. Approximately 40 cm distance has proven to be practical.

It is possible in the manner described above, to determine, one after the other, the oxygen content in the steel melt 3, the oxygen content in the slag layer 2, and the surface level of the bath (boundary layer 10).

Figure 4:
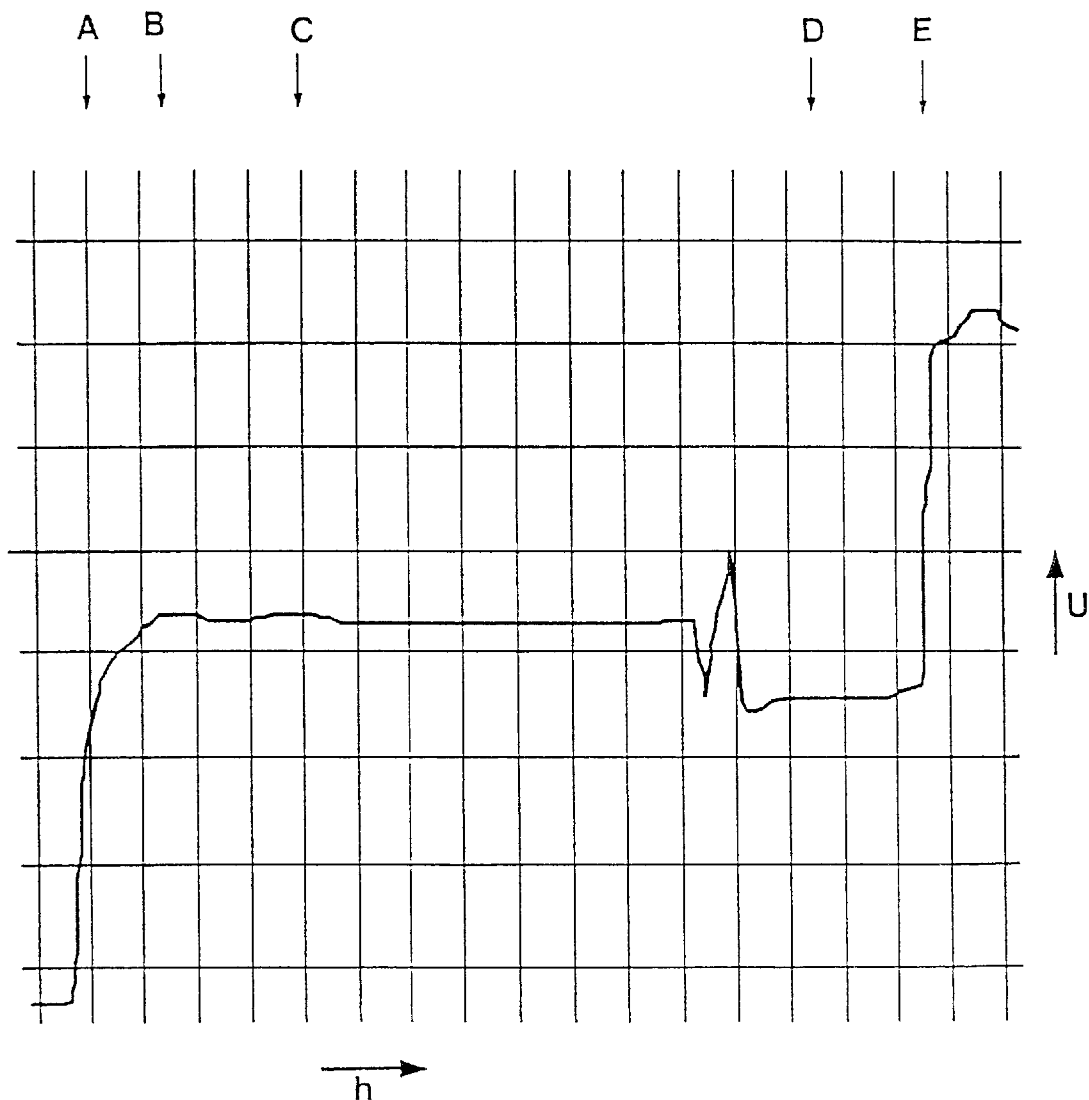
FIG. 4 is the progression of the electrochemical voltage during the measurement process.

In FIG. 4, the voltage progression during the measurement is depicted. The height h of the probe is represented therein on the abscissa and the measured electrochemical voltage U is represented on the ordinate. On the basis of the voltage, the oxygen partial pressure can be calculated in a generally known way. The individual positions are indicated with the same letters as the corresponding positions in FIG. 3. Position A shows the voltage when the measuring cell 5 and counter electrode 4 are immersed in the steel melt 3, i.e. at the beginning of measurement prior to adjustment of the temperature equilibrium. In position C the measuring cell 5 is located in the steel melt 3, whose oxygen activity is measured. In position D the measuring cell 5 is located in the slag layer 2, while the counter electrode 4 is arranged in the steel melt 3, so that the activity in the slag layer 2 is measured. Position E shows the sharp increase in the voltage when the counter electrode 4 leaves the steel melt 3.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. An immersion sensor for measuring an electrochemical activity of a layer lying on a melt, comprising an electrochemical sensor arranged on a support, the sensor comprising an electrochemical measuring cell (5) and a counter electrode (4), the measuring cell (5) and counter electrode (4) having a protective cover (7; 8), and the measuring cell (5) being arranged spaced at a distance above the counter electrode (4) in an immersed position of the sensor.

2. The immersion sensor according to claim 1, wherein the support is constructed as a support tube (1), the measuring cell (5) is arranged on or in a side wall of the support tube (1), and the counter electrode (4) is arranged on an immersion end of the support tube (1).

3. The immersion sensor according to claim 2, wherein the measuring cell (5) is arranged in an opening in the side wall of the support tube (1).

4. The immersion sensor according to claim 1, wherein the support is constructed as a support tube (1), the measuring cell (5) and the counter electrode (4) are arranged on an immersion end of the support tube (1), and the counter electrode (4) is arranged on a holder (9), which is attached on the immersion end of the support tube (1).

5. The immersion sensor according to claim 1, wherein the distance between the measuring cell (5) and the counter electrode (4) amounts to at least 2 cm.

6. The immersion sensor according to claim 1, wherein a thermo-element (6) is arranged on the immersion end of the support.

* * * * *